(12) United States Patent
Den Hartog et al.

(10) Patent No.: US 8,067,603 B2
(45) Date of Patent: Nov. 29, 2011

(54) BENZIMIDAZOLONE AND QUINAZOLINONE DERIVATIVES AS AGONISTS ON HUMAN ORL1 RECEPTORS

(75) Inventors: Jacobus A. J. Den Hartog, Weesp (NL); Gustaaf J. M. Van Scharrenburg, Weesp (NL); Herman H. Van Stuivenberg, Weesp (NL); Tinka Tuinstra, Weesp (NL); Jan-Willem Terpstra, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 2030 days.

(21) Appl. No.: 10/946,177

(22) Filed: Sep. 22, 2004

(65) Prior Publication Data

US 2005/0070528 A1 Mar. 31, 2005

Related U.S. Application Data

(60) Provisional application No. 60/505,613, filed on Sep. 25, 2003.

(51) Int. Cl.
*C07D 211/58* (2006.01)
*A61K 31/454* (2006.01)

(52) U.S. Cl. ........................... 546/199; 514/322

(58) Field of Classification Search .................. 546/184, 546/199; 514/322

See application file for complete search history.

(56) References Cited

U.S. PATENT DOCUMENTS 6,262,066 B1 * 7/2001 Tulshian et al. .............. 514/299

FOREIGN PATENT DOCUMENTS

| WO | WO 9936421 A1 * | 7/1999 |
|----|----|----|
| WO | WO 01/39775 | 6/2001 |
| WO | WO 02/100861 | 12/2002 |

OTHER PUBLICATIONS

Jenck et. al. "A synthetic agonist at the orphanin FQ/nociceptin receptor ORL1: Anxiolytic profile in the rat" Proceedings of the National Academy of Sciences 2000, 97, 4938-4943.*

Wichmann et. al. "Synthesis of (1S,3aS)-8-(2,3,3a,4,5,6-hexahydro-1H-phenalen-1-yl)-1-phenyl-1,3,8-triaza-spiro[4.5]decan-4-one, a potent and selective orphanin FQ (OFQ) receptor agonist with anxiolytic-like properties" European Journal of Medicinal Chemistry 2000, 35, 839-851.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Jones et. al. "5X-Guanidinonaltrindole, a highly selective and potent k-opioid receptor antagonist" European Journal of Pharmacology 396, 2000, 49-52.*
Yoon et. al. "Roles of opioid receptor subtypes on the antinociceptive effect of intrathecal" Neuroscience Letters 441 (2008) 125-128.*
Zaveri et al., "Characterization of Opiates, Neuroleptics, and Synthetic Analogs at ORL1 and Opioid Receptors": *European Journal of Pharmacology*, 428:29-36 (2001).
International Search Report for PCT Application No. PCT/EP2004/052275, 2004.

* cited by examiner

*Primary Examiner* — David K O Dell
(74) *Attorney, Agent, or Firm* — Finnegan, Henderson, Farabow, Garrett & Dunner, L.L.P.

(57) ABSTRACT

The invention relates to a group of novel benzimidazolone and quinazolinone derivatives which are agonists on human ORL1 (nociceptin) receptors. The invention also relates to the preparation of these compounds, to pharmaceutical compositions containing a pharmacologically active amount of at least one of these imidazolone and quinazolinone derivatives as an active ingredient, as well as to the use of these pharmaceutical compositions for the treatment of disorders in which ORL1 receptors are involved. The invention relates to compounds of the general formula (1):

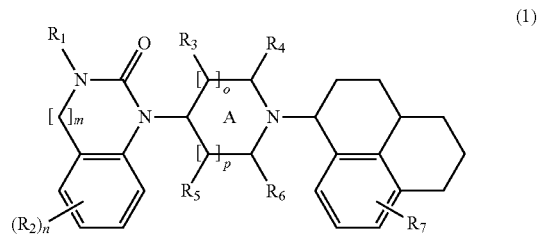

(1)

wherein the symbols have the meanings as given in the description.

7 Claims, No Drawings

BENZIMIDAZOLONE AND QUINAZOLINONE DERIVATIVES AS AGONISTS ON HUMAN ORL1 RECEPTORS

CROSS REFERENCE TO RELATED APPLICATION

This application claims the priority of European Patent Application No. 03 103551.2, filed on Sep. 25, 2003, and the benefit of U.S. Provisional Application No. 60/505,613, filed Sep. 25, 2003, the content of both of which is incorporated herein by reference.

The present invention relates to a group of novel benzimidazolone and quinazolinone derivatives which are agonists on human ORL1 (nociceptin) receptors. The invention also relates to the preparation of these compounds, to pharmaceutical compositions containing a pharmacologically active amount of at least one of these imidazolone and quinazolinone derivatives as an active ingredient, as well as to the use of these pharmaceutical compositions for the treatment of disorders in which ORL1 receptors are involved.

The invention relates to the use of a compound disclosed herein for the manufacture of a medicament giving a beneficial effect. A beneficial effect is disclosed herein or apparent to a person skilled in the art from the specification and general knowledge in the art. The invention also relates to the use of a compound of the invention for the manufacture of a medicament for treating or preventing a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medicament.

The 'Opoid Receptor-Like 1' (ORL1) receptor was identified from a human cDNA library. It was established that this 'orphan receptor' has a close homology with μ-, κ- and δ-opoid receptors (Mollereau et al., *FEBS Lett.*, 341, 33-38, 1994; Bunzow et al., *FEBS Lett.*, 347, 284-288, 1994). Despite its close sequential and structural resemblance with opioid receptors, classical opioid receptor ligands do not interact with ORL1 receptors. In 1995 a 17-amino acid neuropeptide was purified from brain extracts, and subsequently shown to be the natural ligand of the G protein-coupled ORL1 receptor (Reinscheid et al., *Science*, 270, 792-794, 1995; Meunier et al., *Nature*, 377, 532-535, 1995). This peptide was named orphanin FQ or nociceptin. It does not bind to the three traditional opioid receptors. These findings triggered substantial research into the functional role of, and novel ligands for, the ORL1 receptor.

That resulted in several hundreds of publications, including several reviews (see e.g. Grond et al., *Anaesthesist*, 51, 996-1005, 2002), and dozens of patent applications, describing both peptide and non-peptide ligands. The described compounds strongly vary in potency for ORL1 receptors, and also in selectivity (ORL1 versus μ-opiate receptors). As μ-opiate receptors are widely distributed throughout the body, a lack of selectivity might lead to a range of undesired opiate-like side-effects such as sedation, respiratory depression, tolerance and dependence (*Drug News Perspect.*, 14, 335, 2001). The in vivo pharmacodynamic and pharmacokinetic properties of the described compounds are likewise strongly variable.

A number of the ORL1 related patent applications concern benzimidazolone derivatives: e.g. WO 98/54168, WO 99/36421, WO 00/006545, WO 00/08013, WO 01/39775 and U.S. Ser. No. 20020128288. Of the latter, WO 01/39775 is closest to the present invention. However, the benzimidazolone derivatives described therein do not seem to meet the criteria generally acknowledged to be of importance for useful therapeutic agents. They are characterized by:
(1) modest potency (affinities for ORL1 receptors in the range of 166-1252 nM);
(2) little selectivity towards μ-opiate receptors (affinities in the range of 19-457 nM);
(3) no evidence for availability after oral administration, and
(4) no evidence for CNS-availability.

The most potent ORL1 agonist described is Ro 64-6198. This compound does not contain a benzimidazolone moiety but has a spiro core instead (see: EP0856514; Eur. J. Med. Chem., 35 (2000) 839-851 and Proc. Natl. Acad. Sci. USA., 2000, 97, 4938). Ro 64-6198 is cited as a potent and selective compound easily penetrating the Blood Brain Barrier. However, in spite of its favourable in vitro binding data, the in vivo profile of this ligand shows some drawbacks:
(1) it is less efficacious in anxiety models than predicted on basis of the in vitro data
(2) the therapeutic window between the desired efficacy as an ORL1 agonist and the undesired opiate side-effects in vivo is less than predicted on basis of the in vitro data.

The teachings on the benzimidazolone derivatives and Ro 64-6198 quoted above do not indicate directions on how to improve the in vivo pharmacological profile of the best compounds described. In a review on the subject matter ("Characterisation of opiates, neuroleptics, and synthetic analogs at ORL1 and opioid receptors", Eur. J. Pharmacol., 428, 29-36, 2001) Zaveri et al., conclude: "In the absence of a model of a small molecule in the active site, or a crystal structure of the small-molecule-bound ORL1 receptor, one must be very careful in evaluating SAR's among different classes of ORL1 receptor ligands, even those with very close structural similarities"

Surprisingly, it has now been found that in a series of benzimidazolone and quinazolinone derivatives with novel combinations of substituents, a group of compounds was shown to have a high affinity for human ORL1 receptors. Moreover, these compounds show an excellent selectivity for ORL1 receptors relative to μ-opiate receptors, are readily available after oral administration and do penetrate the blood-brain-barrier. The in vitro and in vivo pharmacological profile of several of these compounds are superior to that of Ro 64-6198, in particular with respect to the therapeutic window between the desired efficacy as an ORL1 agonist and the undesired opiate side-effects in vivo. The invention relates to compounds of the general formula (1):

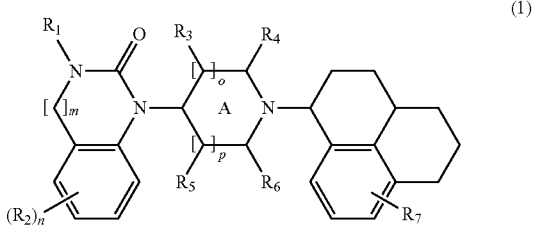

wherein:
$R_1$ represents H, alkyl(1-6C), alkyl(1-3C)cycloalkyl(3-6C), carbalkoxy(2-7C) or acyl(2-7C),
$[\ ]_m$ symbolizes —$(CH_2)_m$— wherein m is either 0 or 1,
$R_2$ represents halogen, $CF_3$, alkyl(1-6C), alkyl(1-3C)cycloalkyl(3-6C), phenyl, amino, aminoalkyl(1-3C), alkyl(1-

3C)amino, dialkyl(1-3C)amino, cyano, cyanoalkyl(1-3C), hydroxy, hydroxyalkyl(1-3C), (1-3C)alkoxy, OCF$_3$, acyl (2-7C), trifluoroacetyl, aminocarboxyl, (1-3C)alkylsulfonyl or trifluoro-methylsulphonyl, and n is an integer from 0-4, with the proviso that when n is 2, 3 or 4, the R$_2$ substituents may be either the same or different, A is a saturated or partially unsaturated ring

[ ]$_o$ and [ ]$_p$ represent —(CH$_2$)$_o$— and —(CH$_2$)$_p$— respectively, with the proviso that also the meaning —CH— is possible when A is a partially unsaturated ring, and o and p independently are either 0, 1 or 2, R$_3$, R$_4$, R$_5$ and R$_6$ independently represent hydrogen, alkyl(1-3C), alkyl(1-3C)cyclo-alkyl(3-6C), CH$_2$OH or (R$_3$ and R$_5$) or (R$_3$ and R$_6$) or (R$_4$ and R$_5$) or (R$_4$ an R$_6$) together can form an alkylene bridge of 1 to 3 carbon atoms, with the proviso that when o is 2, R$_3$ is hydrogen, and when p is 2, R$_5$ is hydrogen, R$_7$ represents H, halogen, CF$_3$, alkyl(1-6C), alkyl(1-3C)cycloalkyl(3-6C), amino, aminoalkyl(1-3C), alkyl(1-3C)amino, dialkyl(1-3C)amino, hydroxy, hydroxyalkyl(1-3C), (1-3C)alkoxy, OCF$_3$, acyl(2-7C), aminocarboxyl or (1-3C) alkylsulfonyl, and pharmacologically acceptable salts and prodrugs thereof.

To the invention belong all compounds having formula (1), racemates, mixtures of diastereomers and the individual stereoisomers. Thus compounds in which the substituents on potentially asymmetrical carbon atoms are in either the R-configuration or the S-configuration belong to the invention. Also prodrugs, i.e. compounds which when administered to humans by any known route, are metabolised to compounds having formula (1), belong to the invention. Prodrugs are bioreversible derivatives of drug molecules used to overcome some barriers to the utility of the parent drug molecule. These barriers include, but are not limited to, solubility, permeability, stability, presystemic metabolism and targeting limitations (J. Stella, "Prodrugs as therapeutics", *Expert Opin. Ther. Patents*, 14(3), 277-280, 2004). In particular this relates to compounds with primary or secondary amino or hydroxy groups. Such compounds can be reacted with organic acids to yield compounds having formula (1) wherein an additional group is present which is easily removed after administration, for instance, but not limited to amidine, enamine, a Mannich base, a hydroxyl-methylene derivative, an O-(acyloxymethylene carbamate) derivative, carbamate, ester, amide or enaminone. A prodrug is an inactive compound, which when absorbed is converted into an active form (Medicinal Chemistry: Principles and Practice, 1994, ISBN 0-85186-494-5, Ed.: F. D. King, p. 216).

The invention particularly relates to compounds having formula (1) wherein: A is a saturated ring, R$_1$ represents hydrogen, alkyl(1-3C), or acyl(2-4C), R$_3$, R$_4$, R$_5$ and R$_6$ independently represent hydrogen or alkyl(1-3C) or (R$_3$ and R$_5$) or (R$_3$ and R$_6$) or (R$_4$ and R$_5$) or (R$_4$ an R$_6$) together can form an alkylene bridge of 1 to 3 carbon atoms, with the proviso that when o is 2, R$_3$ is hydrogen, and when p is 2, R$_5$ is hydrogen, R$_7$ represents H, halogen, CF$_3$, alkyl(1-3C), amino, aminoalkyl(1-3C), alkyl(1-3C)amino, dialkyl(1-3C) amino, hydroxy, (1-3C)alkoxy or OCF$_3$, and R$_2$, m, n, o and p have the meanings as given above.

More particular the invention relates to compounds of formula (1) wherein: A is a saturated ring, m=0, n=0 or 1, o=1, p=1, R$_1$=H or acetyl, R$_2$ represents halogen, CF$_3$, alkyl(1-3C), amino, cyano, OCH$_3$ or OCF$_3$, R$_3$, R$_4$, R$_5$ and R$_6$ independently represent hydrogen or alkyl(1-2C) or (R$_4$ and R$_6$) together can form an alkylene bridge of 1 to 2 carbon atoms and R$_7$ represents H, halogen, CF$_3$, alkyl(1-3C), amino, hydroxy or OCF$_3$.

Even more preferred is the compound having formula (2) and its stereoisomers. Below, this compound will be referred to as 'example 1'.

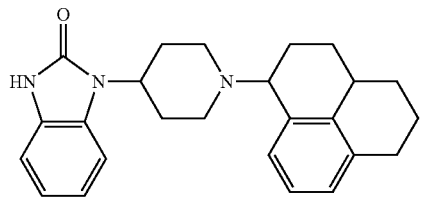

(2)

The compounds of the invention can be brought into forms suitable for administration by means of usual processes using auxiliary substances and/or liquid or solid carrier materials.

Pharmaceutically acceptable salts may be obtained using standard procedures well known in the art, for example by mixing a compound of the present invention with a suitable acid. Suitable acid addition salts can be formed with inorganic acids such as hydrochloric acid or with organic acids such as fumaric acid.

The compounds of the invention of the general formula (1), as well as the salts thereof, have ORL1 agonistic activity. They are useful in the treatment of disorders in which ORL1 receptors are involved, or that can be treated via manipulation of those receptors. For instance in acute and chronic pain conditions, central nervous system disorders, especially, but not limited to amelioration of symptoms of anxiety and stress disorders, depression, various forms of epilepsy, stroke, disorders characterized by impairment of cognition and memory such as Alzheimer's disease, Creutzfeldt-Jacob disease, Huntington's disease, Parkinson's disease, neurorehabilitation (post-traumatic brain lesions); acute brain or spinal cord injury, substance related disorders, including substance use disorders (like dependence and abuse) and substance induced disorders (like substance withdrawal); eating disorders like anorexia nervosa and bulimia nervosa, obesity; gastro-intestinal disorders in particular irritable bowel syndrome, inflammatory bowel disease (Crohn's disease) and ulcerative colitis, urinary tract inflammation, renal disorders characterized by imbalances of water retention/excretion or salt excretion; cardiovascular disorders such as myocardial infarction, arrhythmias, hypertension, thrombosis, anemia, arteriosclerosis, angina pectoris, cutaneous diseases such as urticaria, lupus erythematosus and pruritus; opthalmological disorders like glaucoma; respiratory disorders including chronic obstructive pulmonary disease, bronchitis and cystic fibrosis; diseases of the immune system, and viral infections.

Compounds of the present invention are generally administered as pharmaceutical compositions which are important and novel embodiments of the invention because of the presence of the compounds, more particularly specific compounds disclosed herein. Types of pharmaceutical compositions that may be used include but are not limited to tablets, chewable tablets, capsules, solutions, parenteral solutions, suppositories, suspensions, and other types disclosed herein or apparent to a person skilled in the art from the specification and general knowledge in the art.

In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

General Aspects of Syntheses

The compounds of the invention and their salts can be obtained according to the general route outlined below in scheme 1:

Scheme 1

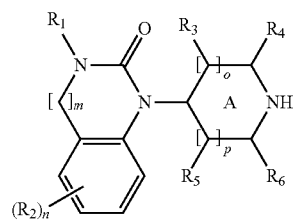

(i)

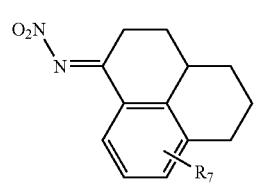

(ii)

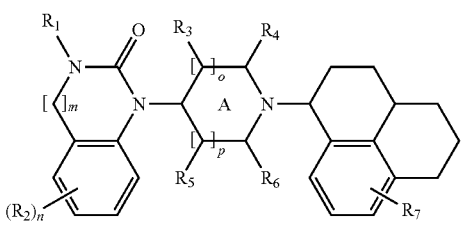

(1)

Starting compounds for this general route are obtained as follows:

benzimidazolones [(i), when m=0] can be synthesized according to the methods described in *J. Med. Chem.*, 30, 814-819, 1987 and WO 99/36421. Quinazolinones [(i), when m=1] can be synthesized according to *Chem. Pharm. Bull.*, 33, 1116-1128, 1985. N-nitro-oximes of (substituted) 2,3,3a,4,5,6-hexahydro-1H-phenalen-1-one (ii) are prepared from the corresponding ketones. These ketones in turn are prepared from the corresponding (substituted) tetralones as described in *Eur. J. Med. Chem.*, 35, 839-851, 2000.

SPECIFIC EXAMPLES OF SYNTHESES

Synthesis of Example 1

A detailed overview of the synthesis of example 1 is given in Scheme 2

Scheme 2

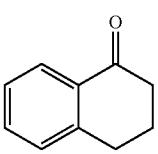
1*

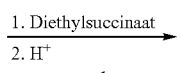
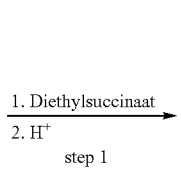

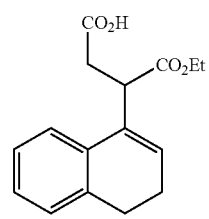

2*

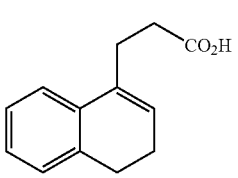

3*

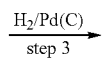

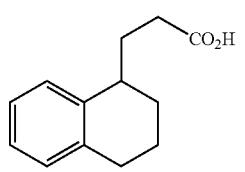

4*

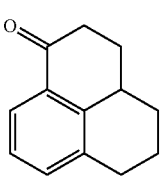

5*

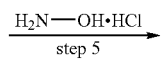

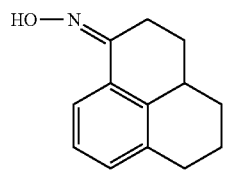

6*

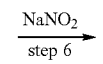

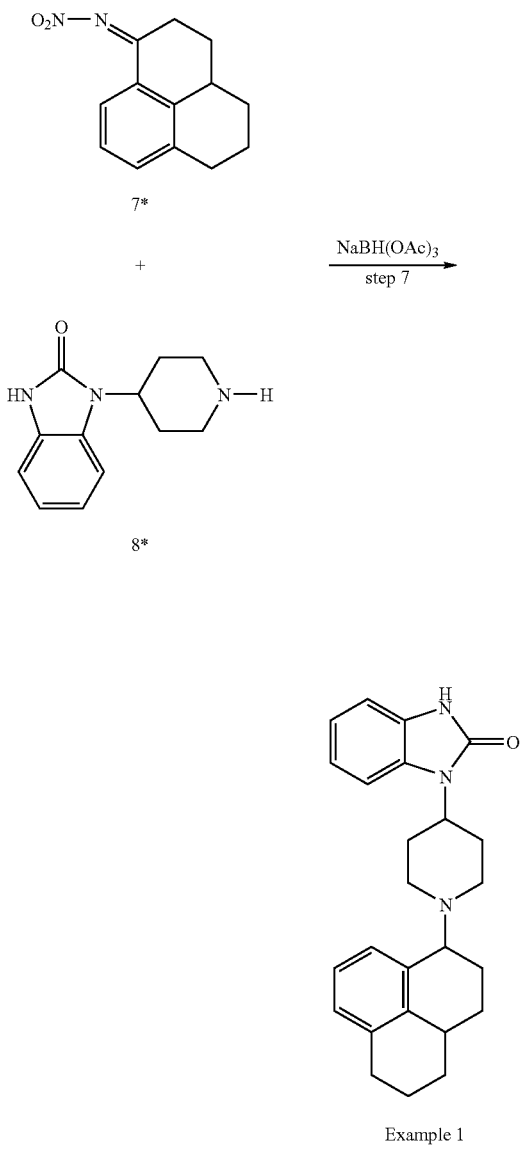

Example 1

The first four steps from scheme 2 were performed according to *Eur. J. Med. Chem.*, 35, 839-851, 2000. Starting with the intermediate compound 5* (see scheme 2), the synthesis is as follows:

Step 5 (scheme 2): A mixture of 52 g (0.28 mole) 2,3,3a,4,5,6-hexahydro-1H-phenalen-1-one (compound 5*), 28.1 g (0.40 mole) hydroxylamine.HCl and 55 g (0.40 mole) sodiumacetate.3H$_2$O in 500 ml 96% ethanol was stirred at 80° C. for 4 hours and for an additional 16 hours at room temperature. The resulting mixture was concentrated in vacuo and 750 ml dichloromethane and 300 ml of a 5% aqueous solution of NaHCO$_3$ were added. The aqueous layer was washed twice with 100 ml dichloromethane, the combined organic layers were washed with 100 ml brine, dried over MgSO$_4$ and concentrated in vacuo.

Step 6 (scheme 2): 58.8 g (representing a quantitative yield) of the resulting off-white solid oxime (compound 6*) was suspended in 600 ml t-butylmethyl ether. At room temperature, to this suspension 230 ml of a solution 41.4 g (0.6 mole) of sodium nitrite in water was added, followed by 290 ml of a solution of 2N sulfuric acid. After stirring at 40° C. for 16 hours, the mixture was cooled to room temperature and 300 ml of a saturated aqueous NaHCO$_3$ solution was added. The aqueous layer was extracted twice with 300 ml t-butylmethyl ether and the combined organic layers were washed with 150 ml brine, dried over MgSO$_4$ and concentrated in vacuo. The resulting brown oil was purified by column chromatography (silicagel) with dichloromethane as eluent. The oily product obtained after concentration in vacuo was triturated with cyclohexane and the resulting precipitate was collected by filtration and dried. The pure NO$_2$-imine (compound 7*) was obtained (34 g, 0.148 mole, 52% yield) as an off-white solid with a melting point of 64-69° C.

Step 7 (scheme 2): a mixture of 6.51 g (30 mmole) 4-(1-benzimidazolone) piperidine (compound 8*, ACROS), 6.9 g (30 mmole) of the NO$_2$-imine (compound 7*) and 5.25 ml di-isopropylethylamine in 450 ml 1,2-dichloro-ethane was heated at 50° C. and stirred under N$_2$ for 16 hours. After cooling to room temperature 12.7 g (60 mmole) NaBH(OAc)$_3$ was added and the resulting mixture was stirred at room temperature under N$_2$ for 24 hours. After concentration of the reaction mixture in vacuo, 500 ml dichloromethane and 500 ml of an aqueous 5% NaHCO$_3$ solution were added under stirring. The aqueous layer was washed twice with 100 ml dichloromethane, the combined organic layers were washed with 100 ml brine, dried over MgSO$_4$ and concentrated in vacuo. The crude product was purified by column chromatography (silicagel) with a mixture of dichloromethane-methanol-ammonia (92:7.5:0.5) as eluent. The pure product was obtained by concentration in vacuo (8.09 g, 21 mmole, 70% yield, melting point 155-158° C.). To 8.09 g (21 mmole) of the pure product, 60 ml ethanol and 2.44 g (21 mmole) fumaric acid were added. Concentration in vacuo of the resulting solution afforded the fumarate salt of example 1 (10.53 g, 21 mmole, quantitative yield) as a white foam with a M$^+$ of 358 m/z and a melting point of 232-234° C.

Synthesis of Example 2

A mixture of 2.31 g (10 mmole) 4-(1-quinazolinone) piperidine and 2.3 g (10 mmole) of the NO$_2$-imine (compound 7*) in 100 ml 1,2-dichloroethane under nitrogen was heated and stirred at 50° C. for 7 hours and for an additional 16 hours at room temperature. Subsequently 4.2 g (20 mmole) NaBH(OAc)$_3$ was added and the resulting mixture was stirred at room temperature under N$_2$ for 24 hours. After concentration of the reaction mixture in vacuo, 200 ml dichloromethane and 200 ml of a 5% aqueous NaHCO$_3$ solution were added under stirring. The aqueous layer was washed twice with 40 ml dichloromethane, the combined organic layers were washed with 40 ml brine, dried over MgSO$_4$ and concentrated in vacuo. The crude product was purified by column chromatography (silicagel) with a mixture of dichloromethane:methanol:ammonia (94.5:5:0.5) as eluent. The pure product resulting after concentration in vacuo (2.5 g, 6.2 mmole) was dissolved in 50 ml of a solution of HCl in ethanol. Concentration in vacuo yielded the HCl salt of example 2 (2.05 g, 4.7 mmole, 47% yield) as a white amorphous solid with a M$^+$ of 402 m/z and a melting point of 172-180° C.

Synthesis of Example 13

A detailed overview of the synthesis of example 13 is given in scheme 3:

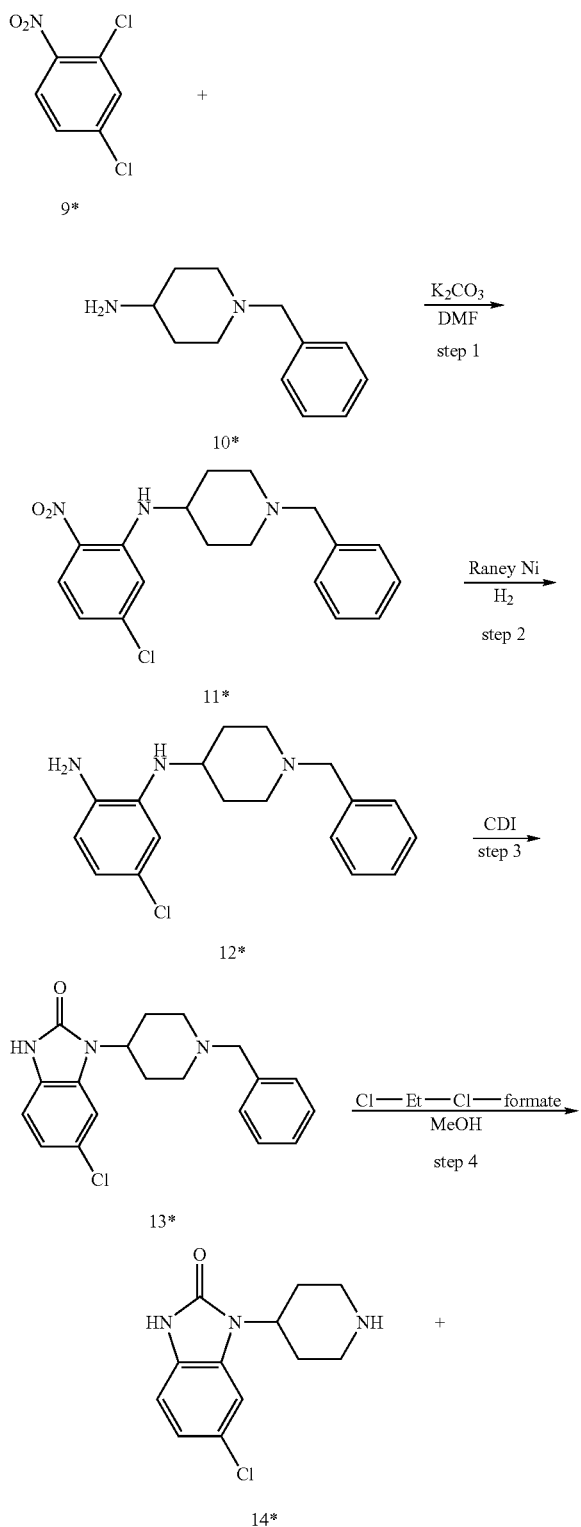

Scheme 3

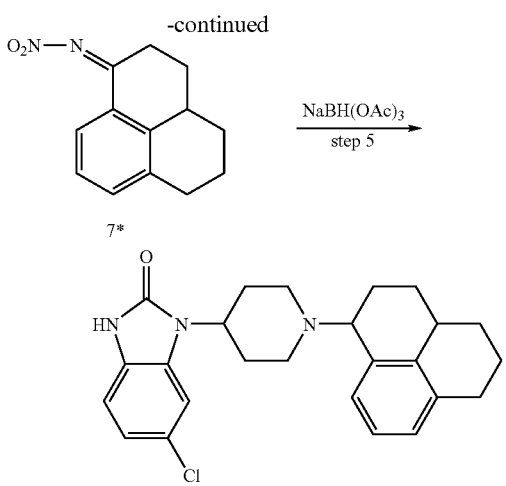

Example 13

Step 1 (scheme 3): a solution of 3.84 g (20 mmole) 2,4-dichloronitrobenzene (compound 9*, Aldrich), 4.1 ml (20 mmole) 4-amino-1-benzylpiperidine (compound 10*, Aldrich), 4.46 g (32 mmole) $K_2CO_3$ in 50 ml dimethylformamide was stirred at 95° C. under $N_2$ for 18 hours. After cooling to room temperature the mixture was poured into water(150 ml)-dichloromethane (250 ml). The aqueous layer was extracted twice with 50 ml dichloromethane and the combined organic layers were washed twice with 50 ml water, dried over $MgSO_4$ and concentrated in vacuo. The resulting crude product was purified by column chromatography (silicagel) with a mixture of dichloromethane:methanol (97:3) as eluent. After concentration in vacuo the pure product was obtained as a yellow oily substance (4.8 g, 13.8 mmole, 69% yield).

Step 2 (scheme 3): a portion of Raney-Ni (Aldrich R 2800 [7440-02-0], ~500 mg) was washed twice with 10 ml 96% ethanol and subsequently added under $N_2$ to a solution of 4.8 g (13.8 mmole) of compound 11* in 200 ml 96% ethanol. The solution was hydrated at room temperature and a pressure of 1 atmosphere for 2.5 hours. The mixture was subsequently filtered over Hyflo, washed with 300 ml 96% ethanol and the filtrate concentrated in vacuo to give quantitative yield of compound 12* as a colored oily substance (4.36 g, 13.8 mmole, 100% yield).

Step 3 (scheme 3): to a solution of 4.36 g (13.8 mmole) of compound 12* the product from the previous step in 200 ml acetonitrile, stirred at room temperature under nitrogen, 3.36 g (20.7 mmole) 1,1'-carbonyldiimidazole (CDI, ACROS) was added. The precipitate, starting to form at 10 minutes and increasing up to 3 hours, was collected by filtration, washed with acetonitrile (200 ml) and dried in vacuo, giving an almost pure compound 13* (3.30 g, 9.7 mmole, 70% yield)

Step 4 (scheme 3): to a suspension of 3.30 g (9.7 mmole) of compound 13* in 90 ml 1,2-dichloroethane, stirred under $N_2$ and cooled to 0° C., a portion of 1-chloroethyl chloroformate (1.17 ml, 10.7 mmole) was added dropwise. After steering at 0° C. for 30 minutes and at 80° C. for 90 minutes, the mixture was cooled again to 0° C. and another portion of 1-chloroethyl chloroformate (1.17 ml, 10.7 mmole) was added dropwise. The mixture was stirred once more at 0° C. for 30 minutes and at 80° C. for 16 hours. After cooling to room temperature the mixture was concentrated in vacuo and 75 ml methanol was added to the residue. The resulting solution was stirred at 65° C. for 1 hour and concentrated in vacuo. After addition of 75 ml dichloromethane to the resulting brown semi-solid it solidified under stirring for 1 hour. The precipitate was collected by filtration, washed with 100 ml dichloromethane and dried. The obtained crude product was purified by column chromatography (silicagel) with a mixture of dichloromethane-methanol-ammonia (92:7.5:0.5) as eluent. After concentration in vacuo compound 14* was obtained as a white solid (1.61 g, 6.4 mmole, 66% yield).

Step 5 (scheme3): a mixture of 1.61 g (6.4 mmole) of compound 14* and 1.47 g (6.4 mmole) of $NO_2$-imine (compound 7*) in 200 ml 1,2-dichloroethane under $N_2$ was heated and stirred at 50° C. for 16 hours. After cooling to room temperature 2.76 g (13 mmole) $NaBH(OAc)_3$ was added and the resulting mixture was stirred at room temperature under $N_2$ for 24 hours. The slightly colored solution was poured on a mixture of 300 ml dichloromethane, 100 ml water and 50 ml aqueous 5% $NaHCO_3$ solution. The aqueous layer was washed twice with 70 ml dichloromethane, the combined organic layers were dried over $MgSO_4$ and concentrated in vacuo. The crude product was purified by column chromatography (silicagel) with a mixture of dichloromethane: methanol:ammonia (92:7.5:0.5) as eluent. The pure product was concentrated in vacuo and solidified upon subsequent co-evaporation with acetonitrile. After stirring in 100 ml di-isopropylether, the precipitate was collected by filtration and dried, leading to example 13 (1.35 g, 3.2 mmole, 50% yield) as a slightly colored pure solid with a M+ of 422 m/z and a melting point of 185-188° C.

By these and comparable methods the following specific examples were synthesized. They are intended to further illustrate the invention in more detail, and therefore are not deemed to restrict the scope of the invention in any way. Structural information of these compounds, all represented by the general formula (1), is presented in the table below.

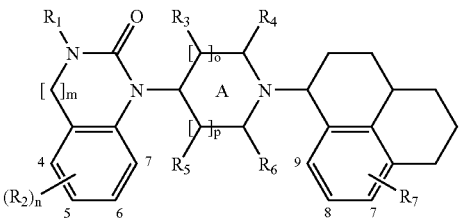

(1)

| nr | $R_1$ | m | $R_2$ | n | A | o | p | $R_3$ | $R_4$ | $R_6$ | $R_5$ | $R_7$ |
|---|---|---|---|---|---|---|---|---|---|---|---|---|
| 1 | H | 0 | — | 0 | sat | 1 | 1 | H | H | H | H | H |
| $1^{S,S}$ | H | 0 | — | 0 | sat | 1 | 1 | H | H | H | H | H |
| $1^{S,R}$ | H | 0 | — | 0 | sat | 1 | 1 | H | H | H | H | H |
| $1^{R,S}$ | H | 0 | — | 0 | sat | 1 | 1 | H | H | H | H | H |
| $1^{R,R}$ | H | 0 | — | 0 | sat | 1 | 1 | H | H | H | H | H |
| 2 | H | 1 | — | 0 | sat | 1 | 1 | H | H | H | H | H |
| 3 | $CH_3$ | 0 | — | 0 | sat | 1 | 1 | H | H | H | H | H |
| 4 | $CH_3$ | 1 | — | 0 | sat | 1 | 1 | H | H | H | H | H |
| 5 | H | 0 | 4-F | 1 | sat | 1 | 1 | H | H | H | H | H |
| 6 | H | 0 | 5-F | 1 | sat | 1 | 1 | H | H | H | H | H |
| 7 | H | 0 | 6-F | 1 | sat | 1 | 1 | H | H | H | H | H |
| 8 | H | 0 | 7-F | 1 | sat | 1 | 1 | H | H | H | H | H |
| 9 | H | 0 | 5-$CF_3$ | 1 | sat | 1 | 1 | H | H | H | H | H |
| 10 | H | 0 | 6-$CF_3$ | 1 | sat | 1 | 1 | H | H | H | H | H |
| 11 | H | 0 | 4-Cl | 1 | sat | 1 | 1 | H | H | H | H | H |
| 12 | H | 0 | 5-Cl | 1 | sat | 1 | 1 | H | H | H | H | H |
| 13 | H | 0 | 6-Cl | 1 | sat | 1 | 1 | H | H | H | H | H |
| 14 | H | 0 | 7-Cl | 1 | sat | 1 | 1 | H | H | H | H | H |
| 15 | H | 0 | 4-$CH_3$ | 1 | sat | 1 | 1 | H | H | H | H | H |
| 16 | H | 0 | 5-$CH_3$ | 1 | sat | 1 | 1 | H | H | H | H | H |
| 17 | H | 0 | 6-$CH_3$ | 1 | sat | 1 | 1 | H | H | H | H | H |
| 18 | H | 0 | 7-$CH_3$ | 1 | sat | 1 | 1 | H | H | H | H | H |
| 19 | H | 0 | 4-$OCH_3$ | 1 | sat | 1 | 1 | H | H | H | H | H |
| 20 | H | 0 | 5-$OCH_3$ | 1 | sat | 1 | 1 | H | H | H | H | H |
| 21 | H | 0 | 6-$OCH_3$ | 1 | sat | 1 | 1 | H | H | H | H | H |
| 22 | H | 0 | 6-OH | 1 | sat | 1 | 1 | H | H | H | H | H |
| 23 | H | 0 | 6-$NHCOCH_3$ | 1 | sat | 1 | 1 | H | H | H | H | H |
| 24 | H | 0 | 6-CN | 1 | sat | 1 | 1 | H | H | H | H | H |
| 25 | H | 0 | 6-$CH_2CN$ | 1 | sat | 1 | 1 | H | H | H | H | H |
| 26 | H | 0 | 6-$SO_2CH_3$ | 1 | sat | 1 | 1 | H | H | H | H | H |
| 27 | H | 0 | 6-$SO_2CF_3$ | 1 | sat | 1 | 1 | H | H | H | H | H |
| 28 | H | 0 | 6-$COCH_3$ | 1 | sat | 1 | 1 | H | H | H | H | H |
| 29 | H | 0 | 6-$COCF_3$ | 1 | sat | 1 | 1 | H | H | H | H | H |
| 30 | H | 0 | 6-$CONH_2$ | 1 | sat | 1 | 1 | H | H | H | H | H |
| 31 | H | 0 | 6-$OCF_3$ | 1 | sat | 1 | 1 | H | H | H | H | H |
| 32 | H | 0 | 6,7-F | 2 | sat | 1 | 1 | H | H | H | H | H |
| 33 | H | 0 | 4-F, 6-$OCH_3$ | 2 | sat | 1 | 1 | H | H | H | H | H |
| 34 | H | 0 | 4-$CH_3$, 6-$OCH_3$ | 2 | sat | 1 | 1 | H | H | H | H | H |
| 35 | H | 0 | — | 0 | sat | 1 | 0 | H | H | H | H | H |
| 36 | H | 0 | — | 0 | sat | 0 | 0 | H | H | H | H | H |
| 37 | H | 0 | — | 0 | sat | 1 | 1 | $CH_3$ | H | H | H | H |
| 38 | H | 0 | — | 0 | sat | 1 | 1 | H | $CH_3$ | H | H | H |
| 39 | H | 0 | — | 0 | sat | 1 | 1 | H | H | H | $CH_3$ | H |

| | | | | | | | | | | | |
|---|---|---|---|---|---|---|---|---|---|---|---|
| 40 | H | 0 | — | 0 | sat | 1 | 1 | H | H | $CH_3$ | H | H |
| 41 | H | 0 | — | 0 | sat | 1 | 1 | H | —$CH_2$—$CH_2$— | H | H |
| 42 | H | 0 | — | 0 | sat | 1 | 1 | H | H | H | H | 8-F |
| 43 | H | 0 | — | 0 | sat | 1 | 1 | H | H | H | H | 7-$CH_3$ |
| 44 | H | 0 | — | 0 | sat | 1 | 1 | H | H | H | H | 8-$CH_3$ |
| 45 | H | 0 | — | 0 | sat | 1 | 1 | H | H | H | H | 9-F |

Pharmacological Assays

The in vitro and in vivo ORL1 receptor agonistic properties of the compounds of the invention, as well as their (lack of) μ-opiate activity, were determined using the methods outlined below.

Affinity for Human ORL1 Receptors

Affinity of the compounds for human ORL1 receptors was determined using the in vitro receptor binding assay described by Ardati et al., *Mol. Pharmacol.*, 51, 816, 1997. Briefly, membrane preparations were obtained from CHO-cells in which the human ORL1 receptor was stably expressed. Membranes were incubated with [$^3$H]-nociceptin in the absence or presence of test compound in different concentrations, diluted in a suitable buffer. Non specific binding was defined as binding remaining in the presence of $10^{-6}$ M nociceptin. Separation of bound radioactivity from free was done by filtration through Packard GF/B glass fiber filters with several washings with ice-cold buffer using a Packard cell harvester. Bound radioactivity was measured with a scintillation counter (Topcount, Packard) using a liquid scintillation cocktail (Microscint 0, Packard). Measured radioactivity was plotted against the concentration of the displacing test compound and displacement curves were calculated by four-parameter logistic regression, resulting in $IC_{50}$ values, i.e. that concentration of test compound by which 50% of the radioligand is displaced. Affinity $pK_i$ values were calculated by correcting the $IC_{50}$ values for radioligand concentration and its affinity for the human ORL1 receptor according to the Cheng-Prusoff equation:

$$pK_i = -\log(IC_{50}/(1+S/K_d))$$

in which the $IC_{50}$ is as described above, S is the concentration [$^3$H]-nociceptin used in the assay expressed in mol/l (typically 0.2 nM), and $K_d$ is the equilibrium dissociation constant of [$^3$H]-nociceptin for human ORL1 receptors (0.4 nM).

The compounds of the invention have a high affinity for ORL1 receptors in the binding assay described above. This property makes them useful in the treatment of disorders in which ORL1 receptors are involved, or that can be treated via manipulation of these receptors.

Affinity for Human μ-Opiate Receptors

Affinity of the compounds for μ-opiate receptors was determined using the in vitro receptor binding assay described by Childers et al, *Eur. J. Pharm* 55, 11, 1979. Briefly, membrane preparations were obtained from CHO-cells in which the human μ-opiate receptor was stably expressed, and were incubated with the [$^3$H]-naloxone in the absence or presence of test-compounds in a concentration range from 10 μM down to 0.1 nM, diluted in a suitable buffer. Non specific binding was defined as binding remaining in the presence of $10^{-7}$ M levallorphan tartrate. Separation of bound radioactivity from free was done as described above, and the affinity of the compounds was calculated in a similar way, using a concentration (S) of 1 nM [$^3$H]-naloxone and with a $K_d$ value of 1.3 nM Most of the compounds of the invention have a low affinity for μ-opiate receptors in the binding assay described above. Thus they are unlikely to evoke the unwanted side effects known to occur with opiates like morphine.

In Vitro ORL1 Receptor Agonism

Activation of the G protein-coupled ORL1 receptor inhibits adenylate cyclase activity and reduces the intracellular concentration of the second messenger cAMP. Using the assay as described by Jenck et al., *Proc. Natl. Acad. Sci. USA*, 97, 4938-4943, 2000, the activity of the compounds on ORL1 receptors was measured. They were demonstrated to be potent agonists.

In Vivo ORL1 Receptor Agonism

After intraperitoneal and/or oral administration the compounds of the invention were shown to be highly active in the Conditioned Ultrasonic Distress Vocalisation (CUDV) procedure as described by Van der Poel et al., *Psychopharmacology*, 97, 147-148, 1989. This demonstrates not only that the compounds have a good bioavailability after oral administration, but also that they cross the Blood-Brain-Barrier. The peptide nociceptin is also active in this assay, but in order to demonstrate its effect, it needs to be administered directly into the brain (by intracerebro-ventricular injection).

ORL1 Agonist Induced Decrease in Blood Pressure

With intervals of 5 minutes rats, anaesthetized by 80 mg/kg i.p. sodium pentobarbital, were administered increasing intravenous doses of ORL1 agonists resulting in a decrease in blood pressure. This decrease is expressed as $ED_{80}$: the dose resulting in a 20% decrease in blood pressure compared to control. In interaction experiments, a single intravenous dose of 2 mg/kg of the opiate antagonist naloxone or 1 mg/kg of the selective ORL1 antagonist J-113397 was given 10 minutes before the first dose of the agonist. This dose of J-113397 was able to completely antagonize the effect of nociceptin. This dose of naloxone is known to antagonize the morphine-induced decrease in blood pressure but was without effect on the nociceptin-induced decrease in blood pressure.

ORL1 Agonist and Morphine Induced Effects on Food Intake

Recent studies have demonstrated that food intake can be pharmacologically regulated by ligands of opiate receptors. Sanger and McCarthy (Increased food and water intake produced in rats by opiate receptor agonists. *Psychopharmacology*, 74(3):217-220, 1981) showed that systemic administration of morphine results in an increase in food intake, an effect which is reversed by the non-selective opiate antagonist naloxone. Furthermore, Ciccocioppo et al. (Reversal of stress- and CRF-induced anorexia in rats by the synthetic nociceptin/orphanin FQ receptor agonist, Ro 64-6198. *Psychopharmacology*, 161(2):113-119, 2002) reported that systemic administration of the ORL1 agonist Ro 64-6198 also increased food intake in rats.

Male Wistar rats were housed singly and had free access to food and water. A single dose of vehicle, Ro 64-6198 (1, 3, 6, 10 mg/kg), Example 1 (0.3, 1, 3, 6, 10 mg/kg) or morphine (1, 3, 10 mg/kg) was administered intraperitoneally and the food removed beyond the reach of the animal. 15 minutes after drug administration, a weighed amount of food (5-6 pellets=25-30 grams) was re-introduced into the animal's cage. The food is then re-weighed 60 and 120 minutes later. All animals were re-used for up to 4 separate experiments with a minimum time interval of 5 days between experiments. Precautions were taken to ensure that no extraneous noise induced any additional stress for the animal. In those experiments where the opiate antagonist naloxone (1, 3, 10 mg/kg) or the ORL1 antagonist J113397 (3, 10, 30 mg/kg) was given prior to agonist (Ro 64-6198, 6 mg/kg; Example 1, 10 mg/kg or morphine, 2 mg/kg) administration, the antagonist was administered intraperitoneally 30 minutes prior to agonist administration. All experimental groups represented a minimum of six animals per group.

Formulations of Compounds as Used in Animal Studies

Formulation of Example 1

For oral (p.o.) administration: to the desired quantity (0.5-15 mg) of the solid Example 1 in a glass tube, some glass beads were added and the solid was milled by vortexing for 2 minutes. After addition of 1 ml of a solution of 1% methylcellulose in water, the compound was suspended by vortexing for 10 minutes. For concentrations up and above 1 mg/ml remaining particles in the suspension were further suspended by using an ultrasonic bath.

For intraperitoneal (i.p.) administration: to the desired quantity (0.5-15 mg) of the solid Example 1 in a glass tube, some glass beads were added and the solid was milled by vortexing for 2 minutes. After addition of 1 ml of a solution of 1% methylcellulose and 5% mannitol in water, the compound was suspended by vortexing for 10 minutes. Finally the pH was adjusted to 7.

Formulation of Example 2

For oral (p.o.) administration: to the desired quantity (0.5-15 mg) of the solid Example 2 in a glass tube, some glass beads were added and the solid was milled by vortexing for 2 minutes. After addition of 1 ml of a solution of 1% methylcellulose in water, the compound was suspended by vortexing for 10 minutes. The pH was adjusted to 7 with a few drops of aqueous NaOH (0.1N). Remaining particles in the suspension were further suspended by using an ultrasonic bath.

For intraperitoneal (i.p.) administration: formulations were obtained analogously to those used for p.o. administration by using 1% methylcellulose with 5% mannitol instead of 1% methylcellulose in water.

Pharmacological Data
In Vitro Affinity for ORL1 and µ-Opiate Receptors, Functional ORL1 Agonism

| Example No. | affinity | | In vitro agonism |
| | ORL1 $pK_i$ | µ-opi $pK_i$ | cAMP assay $pEC_{50}$ |
| --- | --- | --- | --- |
| (rac)-Ro 64-6198 | 9.0 | 7.3 | 8.7 |
| example 1 | 8.4 | 7.0 | 9.6 |
| example $1^{S,S}$ | 8.8 | 7.5 | 9.8 |
| example $1^{S,R}$ | 8.5 | 7.7 | 9.8 |
| example $1^{R,S}$ | 8.7 | 6.8 | 9.8 |
| example $1^{R,R}$ | 7.5 | 6.6 | 8.7 |
| example 2 | 8.2 | 7.3 | 9.5 |
| example 6 | 8.4 | 6.4 | |
| example 7 | 8.2 | 6.9 | 9.2 |
| example 8 | 7.8 | | |
| example 10 | 7.3 | <6.0 | |
| example 13 | 8.1 | 6.6 | 7.1 |
| example 15 | 8.6 | 7.5 | |

-continued

| Example No. | affinity | | In vitro agonism |
| | ORL1 $pK_i$ | µ-opi $pK_i$ | cAMP assay $pEC_{50}$ |
| --- | --- | --- | --- |
| example 21 | 7.3 | | |
| example 31 | 7.5 | | |
| example 32 | 7.4 | <6.0 | |
| example 35 | 7.5 | <6.0 | 9.1 |
| example 41 | 8.5 | 6.8 | |
| example 42 | 7.9 | 6.9 | |
| example 43 | 9.2 | 8.1 | |
| example 45 | 8.4 | 7.5 | |

In Vivo ORL1 Agonism: Anxiolytic Activity

| | In vivo agonism CUDV* | |
| compound | i.p. $ED_{50}$ mg/kg | p.o. $ED_{50}$ mg/kg |
| --- | --- | --- |
| example 1 | 0.2 | 0.9 |
| (rac)Ro 64-6198 | 1.9 | 2.8 |

*CUDV = Conditioned Ultrasonic Distress Vocalisation;
i.p. = intraperitoneal;
p.o. = per os (oral)

From the data in table above it is evident that example 1 is ten times more potent than Ro 64-6198 when administered by the intraperitoneal route, and three times more potent when given orally.

Effects on Blood Pressure:

| | $ED_{80}$ in µg/kg (dose producing 20% reduction in blood pressure when compared to control values) | | |
| | Compound alone | +1 mg/kg J11397 | +2 mg/kg naloxone |
| --- | --- | --- | --- |
| Example 1 | 356 | 1,138 | 334 |
| Ro 64-6198 | 84 | 264 | 141 |

The data above show that the blood pressure lowering effect of Example 1 (range 10-3000 µg/kg) was antagonized by J-113397 (shift in dose-response from 356 to 1138 µg/kg) but the effect was naloxone insensitive (no shift in dose-response 356 and 334 µg/kg). The effect of Ro-64-6198 (range 10-1000 µg/kg) was antagonized by J-113397 (shift in dose-response from 84 to 264 µg/kg) and the effect at the two highest doses was naloxone sensitive (shift in dose-response from 84 to 141 µg/kg). Apparently Ro 64-6198 has a µ-opiate component.

| Effects on food intake: | | |
| compound | Dose (mg/kg ip) | Mean ± S.E.M. food intake (g) 120 min after ligand administration |
| --- | --- | --- |
| Vehicle | 0 | 0.01 ± 0.002 |
| Morphine | 1.25 | 1.47 ± 0.39 |
| Morphine | 2.5 | 2.18 ± 0.40 |
| Morphine | 5 | 3.50 ± 0.64 |
| Morphine | 10 | 1.13 ± 0.29 |
| Example 1 | 0.3 | 0.05 ± 0.04 |
| Example 1 | 1 | 0.34 ± 0.33 |
| Example 1 | 3 | 0.73 ± 0.36 |

-continued

Effects on food intake:

| compound | Dose (mg/kg ip) | Mean ± S.E.M. food intake (g) 120 min after ligand administration |
|---|---|---|
| Example 1 | 6 | 1.75 ± 0.40 |
| Example 1 | 10 | 1.93 ± 0.50 |
| Ro-64-6198 | 1 | 0.97 ± 0.38 |
| Ro-64-6198 | 3 | 0.67 ± 0.37 |
| Ro-64-6198 | 10 | 2.13 ± 0.53 |
| naloxone | 3 | 0.09 ± 0.09 |
| naloxone | 30 | 0.05 ± 0.001 |
| J113397 | 30 | 0.06 ± 0.003 |

Morphine (1.25, 2.5, 5 and 10 mg/kg), Ro 64-6198 (1, 3 and 10 mg/kg ip) and example 1 (0.3, 1, 3, 6, 10 ip mg/kg) all resulted in a dose-dependent increase in food-intake which was significant in all cases versus the vehicle treated group. Systemic administration of the opiate antagonist naloxone (3 or 30 mg/kg ip) alone and the ORL1 antagonist J113397 (30 mg/kg ip) alone had no effect on food intake.

| | Antagonism of food intake induced by morphine, RO-64-6198 or example 1 | | | |
|---|---|---|---|---|
| | Naloxone (opiate antagonist) | | J-113397 (ORL1 antagonist) | |
| Compound (mg/kg) | Dose (mg/kg) | Intake (g) | Dose (mg/kg) | Intake (g) |
| Morphine (5) | 0 | 2.92 ± 0.38 | — | — |
| Morphine (5) | 0.03 | 2.34 ± 0.66 | — | — |
| Morphine (5) | 0.3 | 1.96 ± 0.59 | — | — |
| Morphine (5) | 3 | 0.45 ± 0.32 | — | — |
| Example 1 (6) | 0 | 1.02 ± 0.30 | 0 | 1.25 ± 0.39 |
| Example 1 (6) | 0.3 | 0.51 ± 0.16 | 3 | 0.15 ± 0.08 |
| Example 1 (6) | 1 | 0.74 ± 0.27 | 10 | 0.08 ± 0.002 |
| Example 1 (6) | 3 | 0.78 ± 0.23 | 30 | 0.07 ± 0.002 |
| Ro-64-6198 (6) | 0 | 1.50 ± 0.53 | 0 | 1.55 ± 0.56 |
| Ro-64-6198 (6) | 0.3 | 1.00 ± 0.35 | 3 | 1.49 ± 0.40 |
| Ro-64-6198 (6) | 3 | 0.73 ± 0.29 | 10 | 1.62 ± 0.39 |
| Ro-64-6198 (6) | 30 | 0.68 ± 0.35 | 30 | 0.85 ± 0.26 |

The increase in food intake following administration of morphine was antagonized in the presence of the opiate receptor antagonist naloxone. The increase in food intake associated with Example 1 was fully antagonized by the ORL1 antagonist J113397 but not by the opiate receptor antagonist naloxone. J113397 failed to (statistically significantly) antagonize the increase in food intake associated with Ro 64-6198, whilst pretreatment with naloxone resulted in a significant reversal of the Ro 64-6198 induction of food intake.

The current data suggest that the increase in food intake associated with Example 1 is mediated by agonism at ORL1 receptors and not opiate receptors. The increase in food intake associated with Ro 64-6198 was partially antagonized by naloxone but not J113397 suggesting that there is an opiate component to Ro 64-6198 which is not present in Example 1. In conclusion, Example 1 acts as a more selective ORL1 agonist compared to Ro 64-6198.

The invention claimed is:

1. A compound of formula (1)

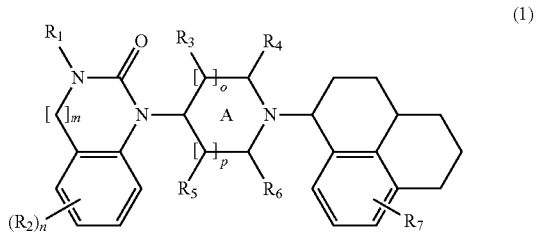

or a pharmaceutically acceptable salt, a stereoisomer, a racemate, or a mixture of diastereoisomers,
wherein:

$R_1$ is chosen from H, alkyl(1-6C), alkyl(1-3C)cycloalkyl (3-6C), carbalkoxy(2-7C) and acyl(2-7C);

$[\ ]_m$ symbolizes —$(CH_2)_m$— wherein m is 0;

$R_2$ is chosen from halogen, $CF_3$, alkyl(1-6C), alkyl(1-3C) cycloalkyl(3-6C), phenyl, amino aminoalkyl(1-3C), alkyl(1-3C)amino, dialkyl(1-3C)amino, cyano, cyanoalkyl(1-3C), hydroxy, hydroxyalkyl(1-3C), (1-3C)alkoxy, $OCF_3$, acyl(2-7C), trifluoroacetyl, aminocarboxyl, (1-3C)alkylsulfonyl and trifluoromethyl sulphonyl, and n is an integer ranging from 0 to 4, with the proviso that when n is 2, 3 or 4, the $R_2$ substituents may be either the same or different;

A is chosen from saturated and partially unsaturated rings;

$[\ ]_o$ and $[\ ]_p$ symbolize —$(CH_2)_o$— and —$(CH_2)_p$— respectively, with the proviso that —CH— is possible when A is a partially unsaturated ring, and o and p independently are chosen 1;

$R_3$, $R_4$, $R_5$ and $R_6$, which are different or identical, are chosen from hydrogen, alkyl(1-3C), alkyl(1-3C)cycloalkyl(3-6C), $CH_2OH$, and ($R_3$ and $R_5$) or ($R_3$ and $R_6$) or ($R_4$ and $R_5$) or ($R_4$ an $R_6$) together can form an alkylene bridge of 1 to 3 carbon atoms; and $R_7$ is chosen from H, halogen, $CF_3$, alkyl(1-6C), alkyl(1-3C)cycloalkyl(3-6C), amino aminoalkyl(1-3C), alkyl(1-3C)amino, dialkyl(1-3C)amino, hydroxy, hydroxyalkyl(1-3C), (1-3C)alkoxy, $OCF_3$, acyl(2-7C), aminocarboxyl, and (1-3C) alkylsulfonyl.

2. The compound as claimed in claim 1, wherein A is a saturated ring; $R_1$ is chosen from hydrogen, alkyl(1-3C), and acyl(2-4C); $R_3$, $R_4$, $R_5$ and $R_6$, which are different or identical, are chosen from hydrogen and alkyl(1-3C), and ($R_3$ and $R_5$) or ($R_3$ and $R_6$) or ($R_4$ and $R_5$) or ($R_4$ an $R_6$) together can form an alkylene bridge of 1 to 3 carbon atoms; and $R_7$ is chosen from H, halogen, $CF_3$, alkyl(1-3C), amino, aminoalkyl(1-3C), alkyl(1-3C)amino, dialkyl(1-3C)-amino, hydroxy, (1-3C)alkoxy and $OCF_3$.

3. The compound as claimed in claim 1, wherein A is a saturated ring; n is 0 or 1; $R_1$ is chosen from hydrogen and acetyl; $R_2$ is chosen from halogen, $CF_3$, alkyl(1-3C), amino, cyano, $OCH_3$ and $OCF_3$; $R_3$, $R_4$, $R_5$ and $R_6$, which are different or identical, are chosen from hydrogen and alkyl(1-2C), and ($R_4$ and $R_6$) together can form an alkylene bridge of 1 to 2 carbon atoms; and $R_7$ is chosen from H, halogen, $CF_3$, alkyl(1-3C), amino, hydroxy, and $OCF_3$.

4. The compound as claimed in claim 1, wherein the compound of formula (1) is a compound of formula (2) or a stereoisomer thereof:

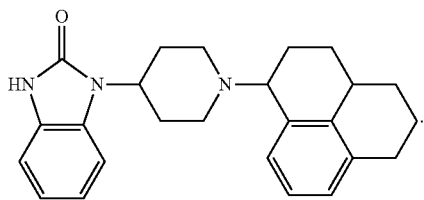
(2)

5. A medicament comprising a compound of formula (1)

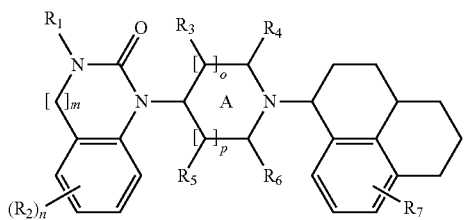
(1)

or a pharmaceutically acceptable salt, a stereoisomer, a racemate, or a mixture of diastereoisomers, wherein:

$R_1$ is chosen from H, alkyl(1-6C), alkyl(1-3C)cycloalkyl (3-6C), carbalkoxy(2-7C) and acyl(2-7C);

$[\ ]_m$ symbolizes —$(CH_2)_m$— wherein m is 0;

$R_2$ is chosen from halogen, $CF_3$, alkyl(1-6C), alkyl(1-3C) cycloalkyl(3-6C), phenyl, amino aminoalkyl(1-3C), alkyl(1-3C)amino, dialkyl(1-3C)amino, cyano, cyanoalkyl(1-3C), hydroxy, hydroxyalkyl(1-3C), (1-3C)alkoxy, $OCF_3$, acyl(2-7C), trifluoroacetyl, aminocarboxyl, (1-3C)alkylsulfonyl and trifluoromethyl sulphonyl, and n is an integer ranging from 0 to 4, with the proviso that when n is 2, 3 or 4, the $R_2$ substituents may be either the same or different;

A is chosen from saturated and partially unsaturated rings;

$[\ ]_o$ and $[\ ]_p$ symbolize —$(CH_2)_o$— and —$(CH_2)_p$— respectively, with the proviso that —CH— is possible when A is a partially unsaturated ring, and o and p independently are 1;

$R_3$, $R_4$, $R_5$ and $R_6$, which are different or identical, are chosen from hydrogen, alkyl(1-3C), alkyl(1-3C)cyclo-alkyl(3-6C), $CH_2OH$, and ($R_3$ and $R_5$) or ($R_3$ and $R_6$) or ($R_4$ and $R_5$) or ($R_4$ an $R_6$) together can form an alkylene bridge of 1 to 3 carbon atoms; and $R_7$ is chosen from H, halogen, $CF_3$, alkyl(1-6C), alkyl(1-3C)cycloalkyl(3-6C), amino aminoalkyl(1-3C), alkyl (1-3C)amino, dialkyl(1-3C)amino, hydroxy, hydroxyalkyl(1-3C), (1-3C)alkoxy, $OCF_3$, acyl(2-7C), aminocarboxyl, and (1-3C) alkylsulfonyl.

6. A pharmaceutical composition comprising a pharmacologically active amount of at least one compound of formula (1)

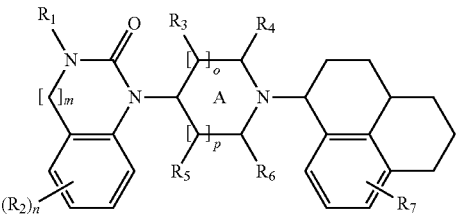
(1)

or a pharmaceutically acceptable salt, a stereoisomer, a racemate or a mixture of diastereoisomers, wherein:

$R_1$ is chosen from H, alkyl(1-6C), alkyl(1-3C)cycloalkyl(3-6C), carbalkoxy(2-7C) and acyl(2-7C);

$[\ ]_m$ symbolizes —$(CH_2)_m$— wherein m is 0;

$R_2$ is chosen from halogen, $CF_3$, alkyl(1-6C), alkyl(1-3C) cycloalkyl(3-6C), phenyl, amino aminoalkyl(1-3C), alkyl(1-3C)amino, dialkyl(1-3C)amino, cyano, cyanoalkyl(1-3C), hydroxy, hydroxyalkyl(1-3C), (1-3C)alkoxy, $OCF_3$, acyl(2-7C), trifluoroacetyl, aminocarboxyl, (1-3C)alkylsulfonyl and trifluoromethyl sulphonyl, and n is an integer ranging from 0 to 4, with the proviso that when n is 2, 3 or 4, the $R_2$ substituents may be either the same or different;

A is chosen from saturated and partially unsaturated rings;

$[\ ]_o$ and $[\ ]_p$ symbolize —$(CH_2)_o$— and —$(CH_2)_p$— respectively, with the proviso that —CH— is possible when A is a partially unsaturated ring, and o and p independently are 1;

$R_3$, $R_4$, $R_5$ and $R_6$, which are different or identical, are chosen from hydrogen, alkyl(1-3C), alkyl(1-3C)cyclo-alkyl(3-6C), $CH_2OH$, and ($R_3$ and $R_5$) or ($R_3$ and $R_6$) or ($R_4$ and $R_5$) or ($R_4$ an $R_6$) together can form an alkylene bridge of 1 to 3 carbon atoms; and $R_7$ is chosen from H, halogen, $CF_3$, alkyl(1-6C), alkyl(1-3C)cycloalkyl(3-6C), amino aminoalkyl(1-3C), alkyl (1-3C)amino, dialkyl(1-3C)amino, hydroxy, hydroxyalkyl(1-3C), (1-3C)alkoxy, $OCF_3$, acyl(2-7C), aminocarboxyl, and (1-3C) alkylsulfonyl.

7. A method of preparing a pharmaceutical composition comprising: combining a compound of formula (1)

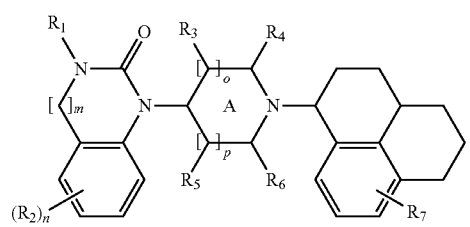
(1)

or a pharmaceutically acceptable salt, a stereoisomer, a racemate, or a mixture of diastereoisomers, wherein:

$R_1$ is chosen from H, alkyl(1-6C), alkyl(1-3C)cycloalkyl (3-6C), carbalkoxy(2-7C) and acyl(2-7C);

$[\ ]_m$, symbolizes —$(CH_2)_m$— wherein m is 0;

$R_2$ is chosen from halogen, $CF_3$, alkyl(1-6C), alkyl(1-3C) cycloalkyl(3-6C), phenyl, amino aminoalkyl(1-3C), alkyl(1-3C)amino, dialkyl(1-3C)amino, cyano, cyanoalkyl(1-3C), hydroxy, hydroxyalkyl(1-3C), (1-3C)alkoxy, $OCF_3$, acyl(2-7C), trifluoroacetyl, aminocarboxyl, (1-3C)alkylsulfonyl and trifluoromethyl sulphonyl, and n is an integer ranging from 0 to 4, with the proviso that when n is 2, 3 or 4, the $R_2$ substituents may be either the same or different;

A is chosen from saturated and partially unsaturated rings;

$[\ ]_o$ and $[\ ]_p$ symbolize $-(CH_2)_o-$ and $-(CH_2)_p-$ respectively, with the proviso that —CH— is possible when A is a partially unsaturated ring, and o and p independently are 1;

$R_3$, $R_4$, $R_5$ and $R_6$, which are different or identical, are chosen from hydrogen, alkyl(1-3C), alkyl(1-3C)cycloalkyl(3-6C), $CH_2OH$, and ($R_3$ and $R_5$) or ($R_3$ and $R_6$) or ($R_4$ and $R_5$) or ($R_4$ an $R_6$) together can form an alkylene bridge of 1 to 3 carbon atoms; and $R_7$ is chosen from H, halogen, $CF_3$, alkyl(1-6C), alkyl(1-3C)cycloalkyl(3-6C), amino aminoalkyl(1-3C), alkyl(1-3C)amino, dialkyl(1-3C)amino, hydroxy, hydroxyalkyl(1-3C), (1-3C)alkoxy, $OCF_3$, acyl(2-7C), aminocarboxyl, and (1-3C)alkylsulfonyl, with a pharmaceutically acceptable carrier and/or at least one pharmaceutically acceptable auxiliary substance.

* * * * *